(12) United States Patent
Herbst (10) Patent No.: US 7,572,377 B2
(45) Date of Patent: Aug. 11, 2009

(54) EXTRACORPOREAL BLOOD FILTER SYSTEM

(76) Inventor: Daniel Patrick Herbst, Springs 1, Villa 26, Street 5, P.O. Box 102985, Dubai (AE)

(*) Notice: Subject to any disclaimer, the term of this patent is extended or adjusted under 35 U.S.C. 154(b) by 0 days.

(21) Appl. No.: 12/201,771

(22) Filed: Aug. 29, 2008

(65) Prior Publication Data

US 2008/0314834 A1    Dec. 25, 2008

(51) Int. Cl.
*B01D 19/00* (2006.01)
*A61F 2/01* (2006.01)
*C02F 3/00* (2006.01)
*B01D 61/32* (2006.01)

(52) U.S. Cl. .............. 210/637; 210/645; 210/435; 210/436; 210/446; 210/741; 210/497.01; 210/767; 604/6.09; 604/333; 604/405; 604/4.01; 604/5.01; 422/44; 422/45

(58) Field of Classification Search ......... 210/435–436, 210/446, 741, 497.01, 767, 493.5, 206; 604/6.09, 604/333, 405, 4.01, 5.01, 319; 422/44, 45; 123/519; 162/181.6; 211/120

See application file for complete search history.

(56) References Cited

U.S. PATENT DOCUMENTS

| 5,374,257 A | * | 12/1994 | Drainville et al. | 604/319 |
| 5,618,425 A | * | 4/1997 | Mitamura et al. | 210/493.5 |
| 6,451,257 B1 | * | 9/2002 | Flamer | 422/44 |

* cited by examiner

*Primary Examiner*—Krishnan S Menon
*Assistant Examiner*—Marjorie Christian (57) ABSTRACT

A blood filter system used for the sequential filtering of blood while actively removing air bubbles and debris comprising a filter housing with unique conical, or cylindrical shape, a flared inlet port, a unique up and down blood flow path, a multi-stage sequential filter assembly, an active air purge assembly and a unique downspout assembly with outlet port. The filter housing is adapted so that blood passes from the inlet port through the multi-stage sequential filter assembly to the outlet port following an up and down flow path, while its unique shape and angled filters effectively direct any air bubbles and debris up and out of the blood stream toward the active air purge assembly where they are removed.

1 Claim, 7 Drawing Sheets

EXTRACORPOREAL BLOOD FILTER SYSTEM

BACKGROUND OF THE INVENTION

1. Field of the Invention

The present invention relates to a blood filter system for use in connection with the filtration of blood in medical devices such as but not limited to extracorproreal circulation systems used during cardiopulmonary support Procedures. The blood filter system has particular utility in connection with the sequential filtering of blood while actively removing air bubbles and debris.

2. Description of the Prior Art

Blood filter systems for extracorporeal circulations are desirable for eliminating micro-bubble contamination and foreign particles from the patient's systemic circulation. It is critical that during any cardiopulmonary support procedures, there are no free gases, or air bubbles present in the blood returning to the patient. It is also critical that blood contacts the least amount of foreign surfaces and contains the least amount of dilution from the extracorporeal circulation system.

The use of blood filters is known in the prior art. For example: U.S. Pat. No. 4,572,724; U.S. Pat. No. 5,744,047; U.S. Pat. No. 5,540,841; U.S. Pat. No. 5,362,406; U.S. Pat. No. 5,258,127, and U.S. Pat. No. 3,701,433.

While the above-described devices fulfill their respective objectives and requirements, the aforementioned patents do not describe a blood filter system that allows the sequential filtering of blood while actively removing air bubbles and debris.

Accordingly, the prior art for blood filter devices used in extracorporeal circulation systems utilizes a large volume chamber with an inlet and outlet, a single stage micro-pore screen filter placed at 90 degree angles to the blood flow path and a large contact surface area to filter air bubbles and debris from the blood stream.

The large volume chamber provides a decrease in blood flow velocity as blood passes through the filter to allow more time for the buoyant forces of any air bubbles present to act, causing them to rise up and separate from the blood stream.

Additionally, construction of the large volume chamber usually includes rounded walls that force the blood to flow in a circular motion to create centrifugal forces within the filter chamber. The centrifugal forces acting on the various elements of blood cause the more dense Red Blood Cell's to spread out along the filters outer wall, while less dense particles such as air bubbles, accumulate at the chambers center where a purge port is located for easy removal.

Moreover, placement of the single stage micro-pore screen filter at 90 degree angles to the blood flow path as described in the prior art reduces filter efficiency and debris clearance from the filter housing. As air bubbles and debris strike the pleated single stage micro-pore screen head on at 90 degree angles to its flow path, they can become effectively trapped between the pleats and held against the screen by the force of the blood flowing through it. Also, the force of collision caused by the direct impact between air bubbles and the filter medium placed at right angles to its flow path promotes further micro-bubble generation as larger bubbles colliding with the screen break apart and increase the amount of filtration required.

Finally, extracorporeal blood filters rely heavily on the principle that describes the Bubble Point Pressure as a means to separate air bubbles from the blood stream. The Bubble Point Pressure is defined as the amount of pressure required to eject air across a wetted pore. As air bubbles cannot easily pass through a wetted pore, their passage is blocked by the filter screen, which separates them from blood flow exiting the filter unless there exists a sufficiently high pre-screen pressure to force them through. Air bubbles entering the filter accumulate on the proximal surface of the micro-pore screen and obstruct blood flow so as to cause a rise in pre-screen pressure within the filter housing. As air bubble accumulation on the micro-pore screen continues, the pre-screen pressure also continues to rise until such time that the Bubble Point Pressure is reached and air is ejected across the wetted pore.

To avoid this, currently available blood filter systems make use of a large micro-pore screen surface area to increase the number of pores available and thereby reduce the potential risk of reaching the Bubble Point Pressure. Increasing the number of available pores is usually accomplished by tightly folding, or pleating extra screen filter material into the filter housing. This large screen surface area contributes negatively to blood handling as it constitutes the majority of foreign surface available for blood contact activation and also sets the requirement for a larger volume filter housing. Although the addition of extra screen filter material helps reduce the possibility of reaching the Bubble Point Pressure, it also makes the job of ensuring the filter is properly de-aired in a timely fashion during priming more difficult, creating a possible safety hazard for the patient.

In conclusion, the above mentioned disadvantages of the prior art are counterproductive to blood filtration as they may promote the build-up and retention of air bubbles and debris on the micro-pore screen, reduce filter efficiency and exposes the patient to increased risk of embolization.

The currently available single stage micro-pore screen filter as described in the prior art is unable to effectively remove all air bubbles and debris from the extracorporeal blood flow. In addition to the foreign surface contact activation and excessive dilution commonly seen during extracorporeal circulations, inadequate filtration continues to play a major role in the problems associated with cardiopulmonary support procedures. Furthermore, advancements in the science of extracorporeal circulation will likely continue to increase demand on system components and their performance as a means of achieving improved patient outcomes. Therefore, a need exists for an improved blood filter system that can increase filter efficiency while decreasing the amount of foreign contact surface area and priming volume required. In this regard, the present invention while departing from conventional concepts and designs of the prior art, substantially fulfills this need and provides an apparatus primarily developed for the sequential filtering of blood and active removal of air bubbles and debris during extracorporeal circulations.

SUMMARY OF THE INVENTION

In contrast to the design limitations inherent in currently available filters for extracorporeal circulation, the present invention provides an improved blood filter system and method which has all the advantages of the prior art and many novel features that result in a blood filter which is not anticipated, rendered obvious, suggested, or even implied by the prior art either alone, or in any combination thereof.

The present invention describes a method that allows for the sequential filtering of blood while actively removing air bubbles and debris and can include a filter housing with a unique conical, or cylindrical shape, a flared inlet port, a unique up and down blood flow path, a multi-stage sequential filter assembly, an active air purge assembly and a unique downspout assembly with outlet port. The filter housing is adapted so that blood passes from the inlet port through the multi-stage sequential filter assembly to the outlet port following an up and down flow path, while its unique shape and angled filters effectively direct any air bubbles and debris up and out of the blood stream toward the active air purge assembly where they are removed.

The above summary has outlined the more important features of the present invention so that it may be better understood and its contribution to the art may be better appreciated. There are of course additional features of the invention that will be described further and which will form the subject matter of the claims attached.

Numerous objects, features and advantages of the present invention will be readily apparent to those of ordinary skill in the art upon a review of the following detailed description and accompanying illustrations. In this respect, before explaining the preferred embodiments of the present invention in detail, it is to be understood that the invention is not limited in its application to the details of construction and arrangement of its components set forth in the following descriptions, or illustrations. Also, it is to be understood that the terminology used is for the purpose of description and should not be regarded as limiting.

As such, those skilled in the art will appreciate the concept upon which this disclosure is based and that it may be readily utilized for the design of other structures, methods and systems for carrying out the several purposes of the present invention and that the claims should be regarded as including such equivalent constructions insofar as they do not depart from the spirit and scope of the present invention.

It is therefore an object of the present invention to provide a new and improved blood filter system that has all of the advantages of the prior art blood filters and none of the disadvantages.

It is another object of the present invention to provide a new and improved blood filter system that may be easily and efficiently manufactured.

An even further object of the present invention is to provide a new and improved blood filter system that has a low cost of manufacture and which accordingly may allow low prices of sale to the consuming public.

Still another object of the present invention is to provide a new blood filter system that provides in the apparatuses and methods of the prior art some of the advantages thereof, while simultaneously overcoming some of the disadvantages normally associated therewith.

Even still another object of the present invention is to provide a blood filter system for the sequential filtering of blood while actively removing air bubbles and debris from the blood stream. This allows for a blood filter system that can have a smaller micro-pore screen filter contact surface area, reduced total device priming volume, unique shaped filter housing, unique up and down blood flow path, unique multi-stage sequential filter assembly, unique angled placement of the filter material within the blood flow, unique sweeping action of blood flow on the angled filter material, reduced force of collision between air bubbles and the angled filter material, unique active air purge assembly, unique methods of actively removing air bubbles from blood, unique built-in pressure relief valve, unique downspout assembly and a unique method of preventing the filter from becoming deprimed.

These objects together with other various features of novelty that characterize the invention are pointed out with particularity in the claims annexed to and forming a part of this disclosure. For a better understanding of the invention, its operating advantages and specific objects obtained by its uses, reference should be made to the accompanying drawings that illustrate the preferred embodiments of the present invention.

BRIEF DESCRIPTION OF THE DRAWINGS

The present invention is better understood when the following detailed description is referenced to the attached drawings wherein.

DESCRIPTION OF THE PREFERRED EMBODIMENTS

Referring now to the drawings and particularly to FIGS. 1-12, the preferred embodiments of the present invention are shown and generally designated by the reference numerals 10 and 100.

Figure 1:
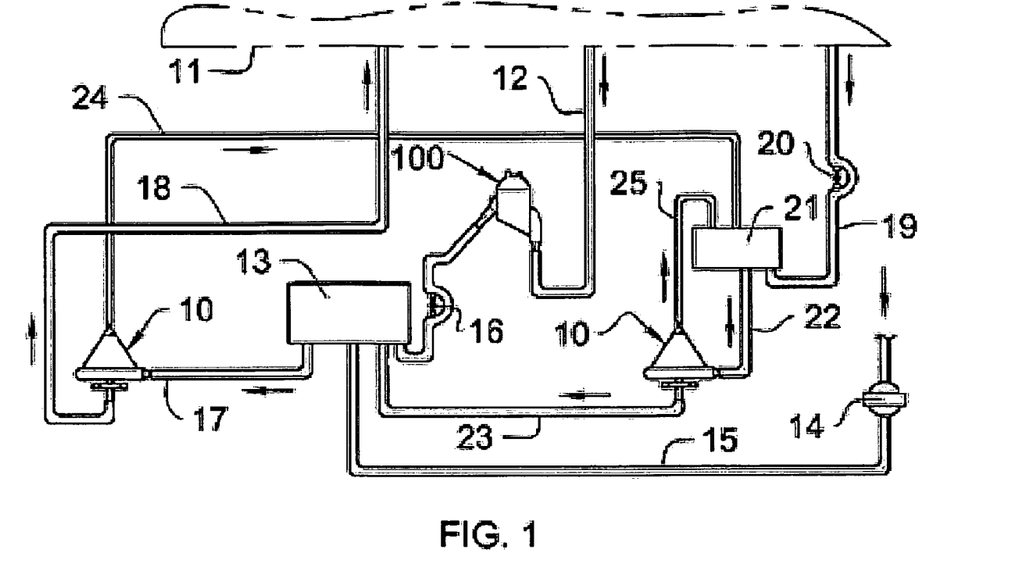
FIG. 1 is a schematic diagram showing the blood filter systems positioned within an extracorporeal circuit in accordance with the principles of the present invention.
Figure 2:
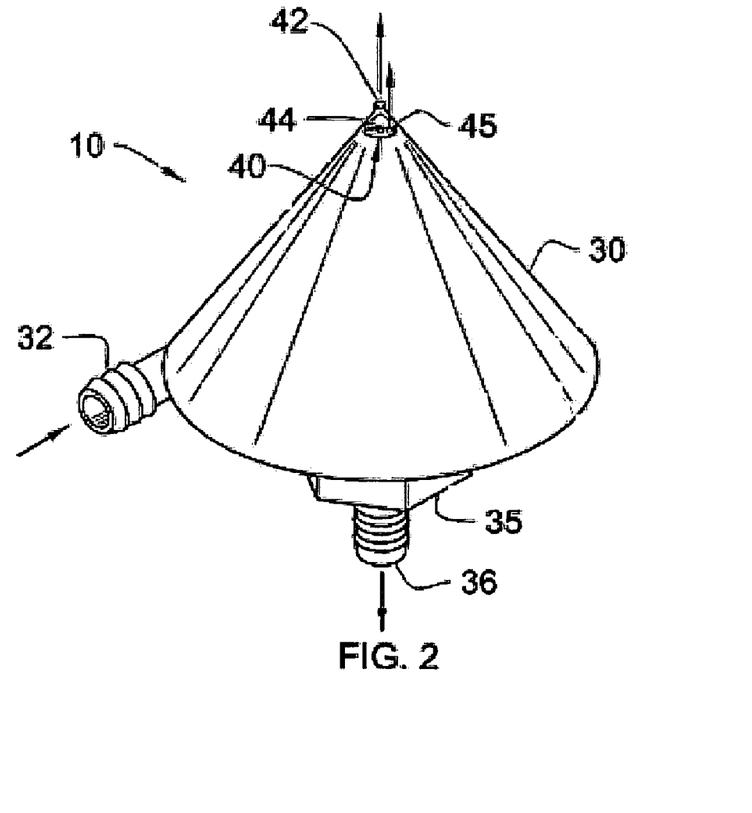
FIG. 2 is a perspective view of the blood filter system of the present invention.

FIG. 1 illustrates the placement of the new and improved blood filter systems 10 and 100 in an extracorporeal circuit used during cardiopulmonary support procedures. One possible bypass circuit is described herewith, but other bypass circuits can also utilize the blood filter systems 10 and 100. In FIG. 1, a pump 16 draws blood from the patient 11 via tube 12 into blood filter system 100 where micro-bubbles, free gases and debris are removed before being pumped into an oxygenating device 13. The oxygenating device 13 removes carbon dioxide from the blood and introduces oxygen from an oxygen filter 14 and tube 15. Blood in oxygenating device 13 is then pumped into blood filter system 10 through tube 17 where micro-bubbles, free gasses and debris are further removed from the blood. Following filtration, blood containing bubbles and debris is purged from blood filter system 10 back to reservoir 21 in tube 24, while filtered blood is returned to patient 11 through tube 18. In the event that there is excess blood where surgery is being performed, it may be removed through tube 19 by pump 20 and delivered to reservoir 21. The excess blood then flows from reservoir 21 through tube 22 to another blood filter system 10 before being routed back to the oxygenating device 13 through tube 23. Additional blood filter systems 10 and 100 can be placed throughout the bypass circuit in any of the drainage, or infusion tubes and is not limited to what is illustrated in FIG. 1.

As best illustrated in FIGS. 2, 3, 4 and 5 blood filter system 10 can have a filter housing 30 with rising inner wall 31, an inlet port 32, a inlet channel 33, a multi-stage sequential filter assembly 60, a purge port 42, an active air purge assembly 40 and a downspout assembly 34. The filter housing 30 can have a generally conical configuration, but other cylindrical or non-cylindrical configurations can be used.

Figure 5:
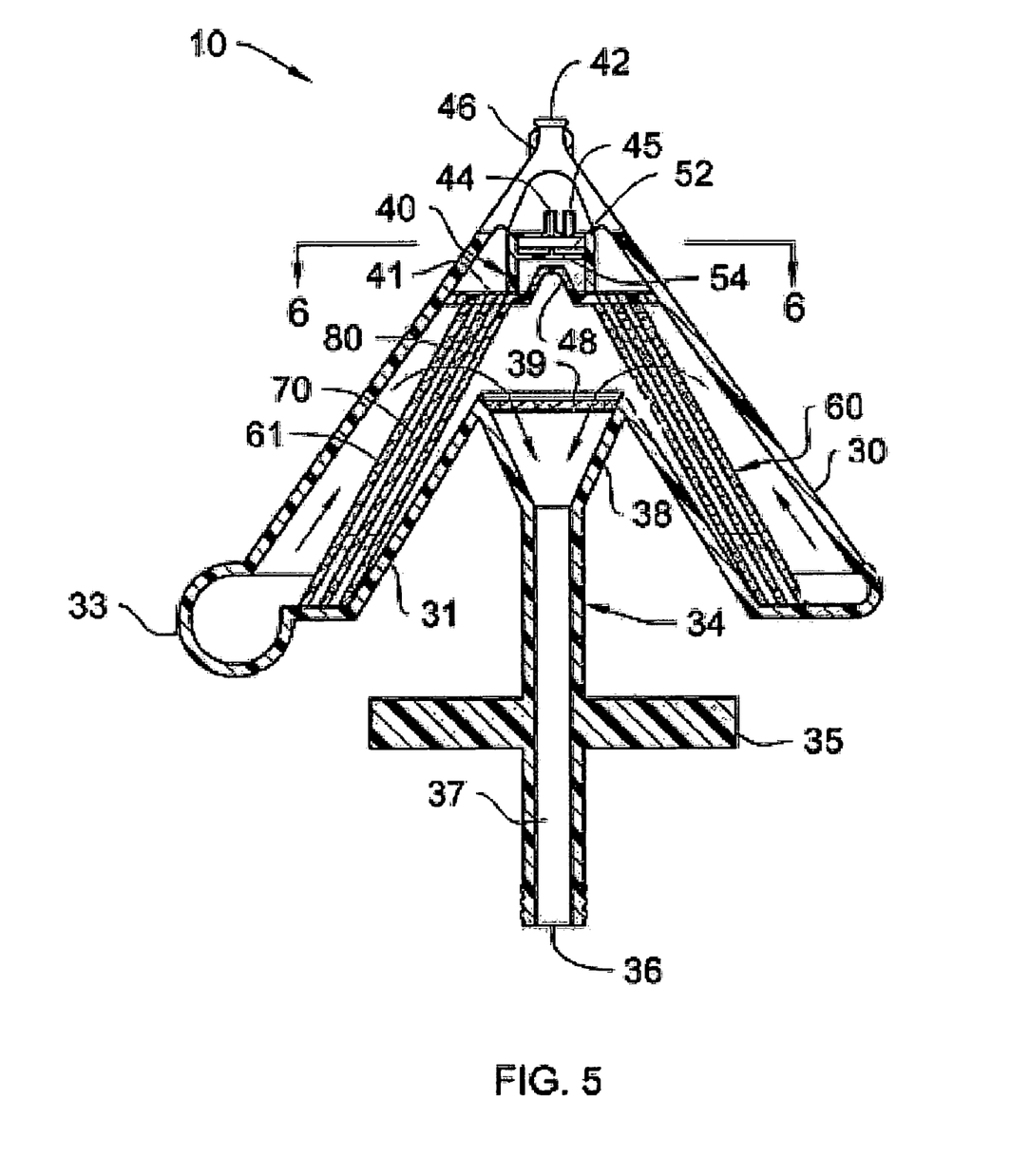
FIG. 5 is a cross-sectional view of the blood filter system of the present invention taken along line 5 in FIG. 4.

As shown in FIG. 5, the multi-stage sequential filter assembly 60 can consist of a first stage filter 61, a second stage filter 70 and a third stage filter 80 all of which can rest on and be secured to each other, the rising inner wall 31 and filter retaining ring 41. The active air purge assembly 40 can be positioned on top of filter housing 30 and may consist of a hydrophobic filter 48, a one-way valve 52, an air removal port 44 and a pressure monitoring port 45. The air removal port 44 may feature a tethered cap which can be moved to close air removal port 44. The downspout assembly 34 can consist of a large diameter funnel 38, a micro-pore screen disk 39, an outflow tube 37, a mounting plate 35 and an outlet port 36. The outflow tube 37 may extend down from the interior of the filter housing 30 to connect the bottom of the large diameter funnel 38 to the outlet port 36. The large diameter funnel 38 may be adapted to retain a disc-shaped micro-pore screen filter 39, which prevents air bubbles and debris from entering the filters outflow tube 37. The disk shaped micro-pore screen filter 39 may be placed within the large diameter funnel 38 so that it remains submerged within the fluid filled downspout assembly at all times. A mounting plate 35 may be positioned along the outflow tube 37 to facilitate the manipulation and securing of the blood filter system 10. The mounting plate 35 may be configured to be self-locking when placed into a mounting device not shown to secure blood filter system 10 while in use.

The multi-stage sequential filter assembly 60 forms the centerpiece of the present invention, representing its primary achievement over that of the prior art.

As illustrated in FIGS. 5, 6, 7 & 8, the multi-stage sequential filter assembly 60 consists of multiple angled micro-pore screen filters 61, 70 & 80 positioned one after the other between the inlet and outlet ports to form in part a major advancement in blood filtration for extracorporeal circulation. Filters 61, 70 & 80 contain a smooth micro-pore filter screens 62, 72 & 82 within support frames 64, 74 & 84. The filter support frames 64, 74 & 84 attach to one another via attachment points 68, 78 & 88, which are designed to limit turbulence as blood flows over them.

Figure 6:
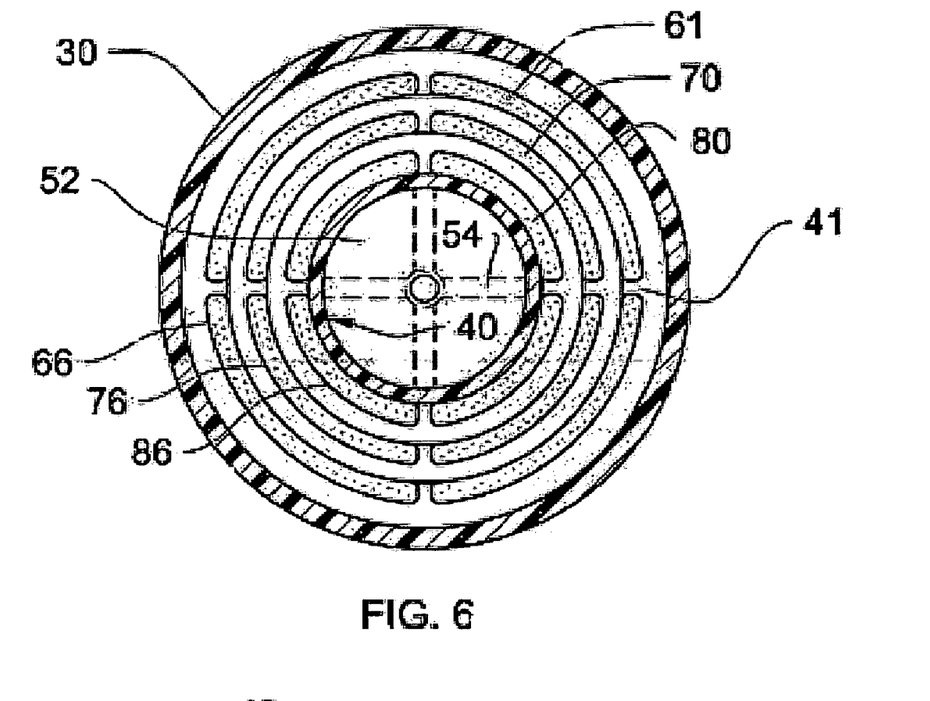
FIG. 6 is a cross-sectional view of the blood filter system of the present invention taken along line 6 in FIG. 5.
Figure 7:
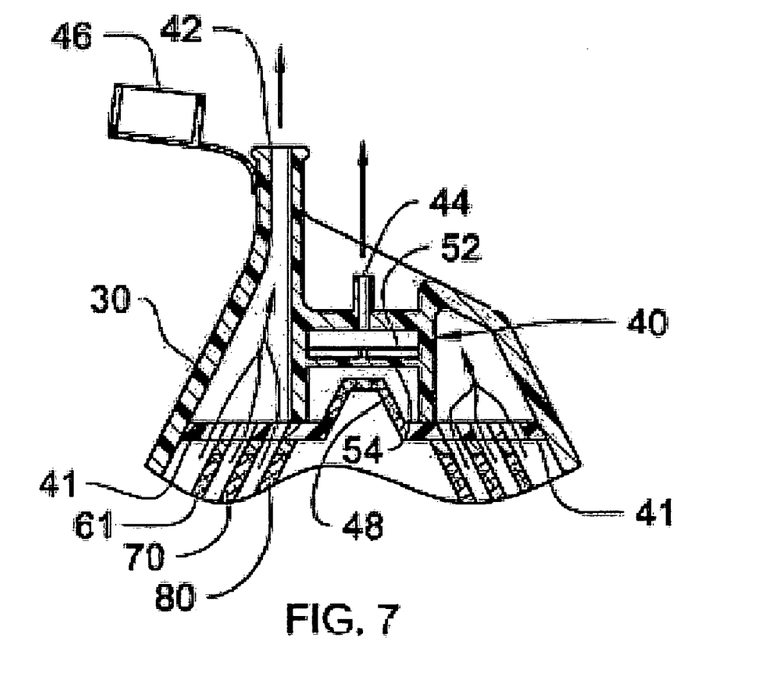
FIG. 7 is a cross-sectional view of the blood filter system of the present invention taken along line 7 in FIG. 4.
Figure 8:
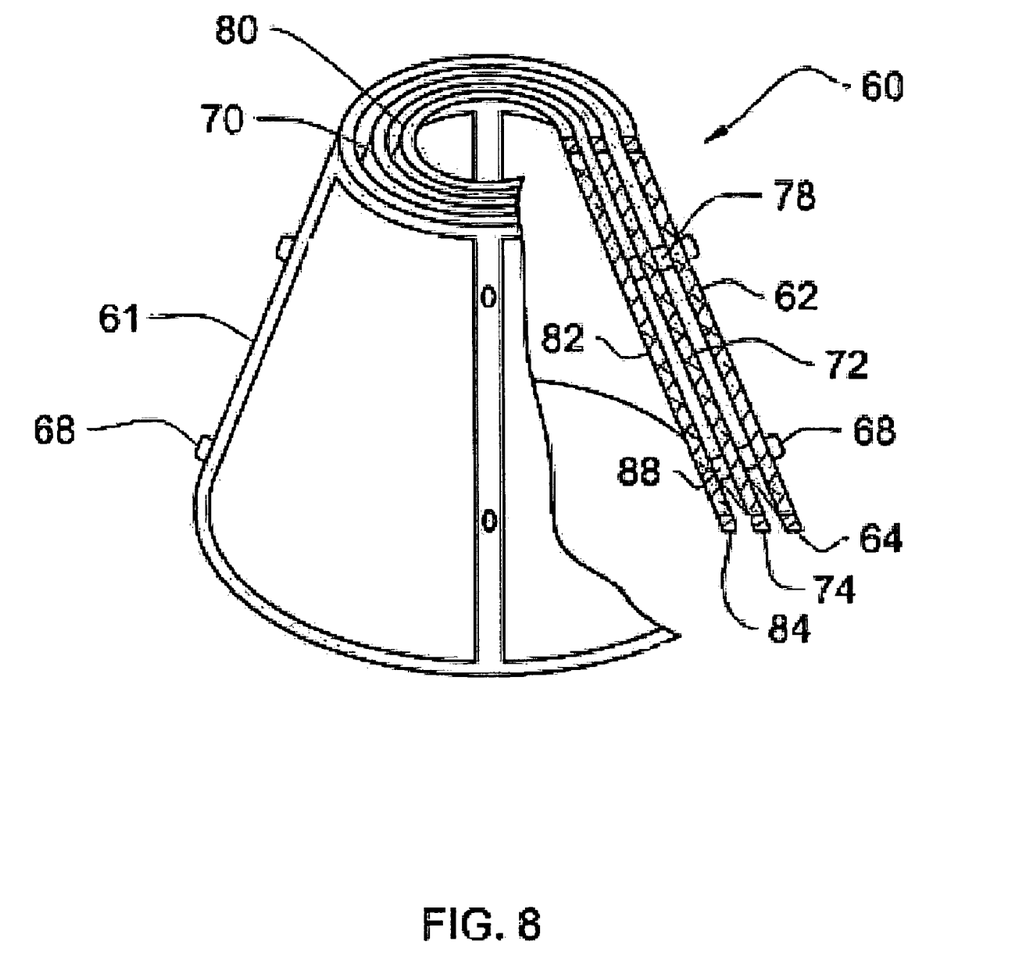
FIG. 8 is a cutaway perspective view of the sequential filter assembly of the blood filter system of the present invention.

As shown in FIGS. 6 & 7, filter retaining ring 41 comprises defined openings 66, 76 & 86. The tops of filters 61, 70 & 80 attach to the underside of filter retaining ring 41 so that the proximal outside surface of smooth micro-pore filter screens 62, 72 & 82 are in fluid communication with defined openings 66, 76, & 86 of filter retaining ring 41.

Blood flow through filter system 10 passes through each filter stage 61, 70 & 80 in sequence to multiply the barrier to air bubble and debris transfer, greatly improving blood filtration and filter efficiency. As long as the Bubble Point Pressure is not exceeded, the wetted pores of filter screens 62, 72 & 82 allow only blood to pass through while preventing the passage of air bubbles and debris. Any air bubbles and debris within the blood are directed up along the outside proximal smooth surface of filter 61 and up through defined opening 66 of filter retaining ring 41 toward purge port 42 where they are removed. In the event that the Bubble Point Pressure is exceeded and air is ejected across the micro-pore filter screen 62 of filter 61, they are then directed to flow up along the outside proximal surface of filter 70 and through defined opening 76 of filter retaining ring 41 toward purge port 42 where they are removed. If the Bubble Point Pressure is again exceeded and air is ejected across the micro-pores of filter screen 72 of filter 70, they are then directed to flow up along the outside proximal surface of filter 80 and through defined opening 86 of filter retaining ring 41 toward purge port 42 where they are removed. If the Bubble Point Pressure is again exceeded and air is ejected across the micro-pore filter screen 82 of filter 80, the buoyant bubbles then flow up due to the low fluid flow velocity at this point created by the large diameter funnel 38. The buoyant bubbles can then come in contact with hydrophobic filter 48 of active air purge assembly 40 where they are removed.

Placement of the multi-stage sequential filters 61, 70 & 80 at angles greater than 90 degrees to the blood flow limits debris trapping and improves its clearance by reducing contact friction between air bubbles, or debris and the angled filter material. Instead of being held against the screen by the force of blood flowing through it, micro-bubbles and debris are more easily swept up along the smooth proximal surface of the angled filters 61, 70 & 80 and through defined openings 66, 76 & 86 toward purge port 42 where they are removed. This unique sweeping action keeps the outside proximal surface of smooth micro-pore screens 62, 72 & 82 free of debris, further enhancing air bubble clearance and filter efficiency.

The angled filters 61, 70 & 80 also help reduce micro-bubble generation within the filter housing by diminishing the acute angle of direct impact and force of collision between air bubbles and the smooth micro-pore filter screens 62, 72 & 82. This reduced force of collision limits air bubble fragmentation to further improve filter efficiency and performance.

The above-mentioned benefits of the multi-stage sequential filter assembly 60 together provide improved filter efficiency, better air bubble and debris clearance and reduced micro-bubble generation over that of the prior art.

Figure 3:
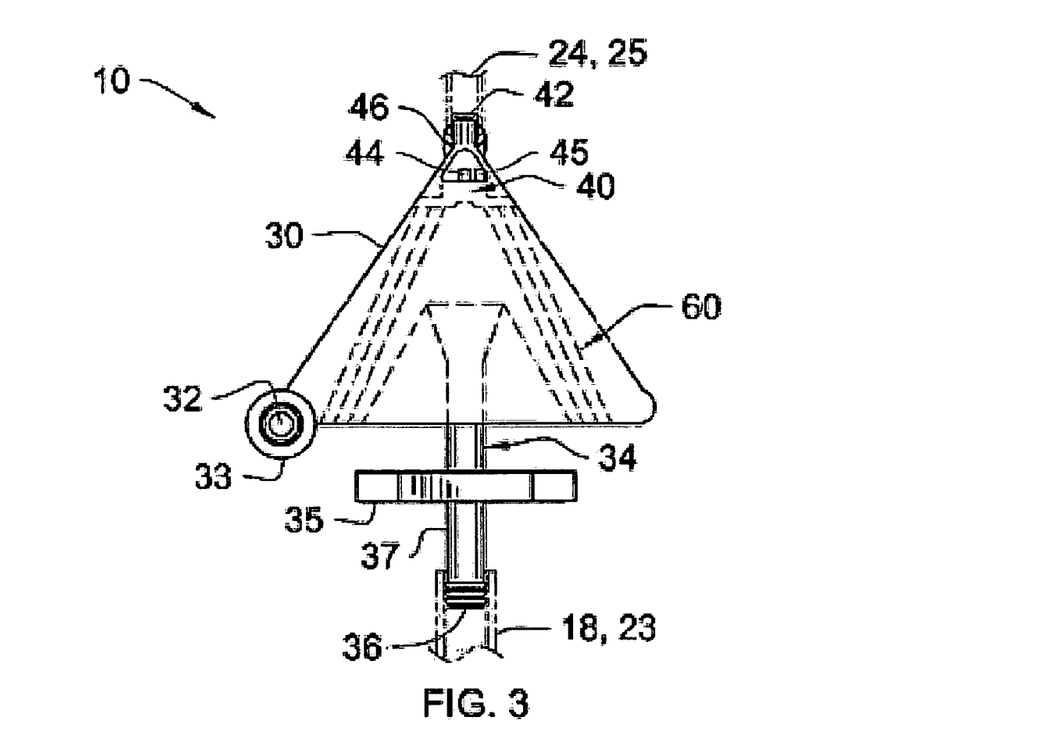
FIG. 3 is a front view of the blood filter system of the present invention.
Figure 4:
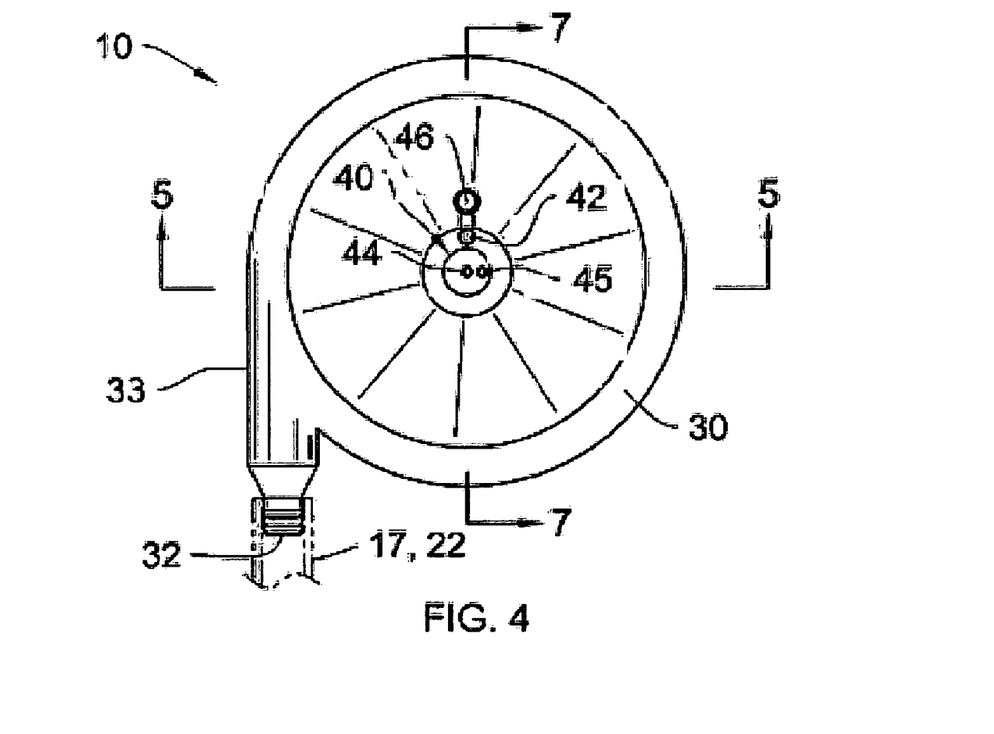
FIG. 4 is a top view of the blood filter system of the present invention.

As shown in FIGS. 3 & 4, inlet port 32 forms a flared inlet channel 33 which is used to decrease blood flow velocity and allow more time for the buoyant forces of any air bubbles present to act. This pre-filter reduction in flow velocity initiates bubble separation from the blood stream before entering the filter housing proper and reduces the number of bubbles that come in contact with the outside proximal surface of the smooth micro-pore screens 62, 72 & 82. In a similar way, FIG. 5 shows the large diameter funnel 38 of downspout assembly 34 also used to decrease flow velocity and improve air bubble separation, but at the filters center directly below the active air purge assembly 40 where bubbles are more easily removed through hydrophobic filter 48. These features together improve air bubble separation and reduce the number that come in contact with the outside proximal surface of micro-pore filter screens 62, 72 & 82 and further improve debris clearance and filter efficiency.

As illustrated in FIGS. 3 & 5, blood entering the filter first flows up in a smooth circular motion between filter housing 30 and rising inner wall 31 to form the first part of a unique up and down flow path. The unique up and down flow path of the present invention improves filter efficiency by augmenting the buoyant forces of air bubbles as they move up in the blood stream toward the filters top. Air bubbles at the filters top then pass through defined openings 66, 76 & 86 of filter retaining ring 41 toward purge port 42 where they are removed, while the filtered blood exiting the multi-stage sequential filter assembly 60 then enters the large diameter funnel 38 where it is directed slowly down through outflow tube 37 and outlet port 36. This completes the up and down flow path which places the buoyant forces of air bubbles and the blood flow exiting the filter in opposite directions of each other to again greatly improve air bubble separation and filter efficiency.

Also shown in FIG. 5, purge port 42 located on top of filter housing 30 and in fluid communication with the interior of filter system 10 forms the upper most portion of the filter housing proper. The active air purge assembly 40 directly above filter retaining ring 41 comprises a hydrophobic filter 48 at its base in fluid communication with the interior of filter housing 30, a one-way valve 52 in fluid communication with the hydrophobic filter 48, an air removal port 44 and pressure monitoring port 45 in fluid communication with the one-way valve 52 and a method to allow the active removal of air bubbles from blood.

FIG. 6 illustrates the filter retaining ring 41 and active air purge assembly 40 at a level above the one-way valve 52. The one-way valve 52 rests on top of support frame 54, preventing it from collapsing back into the active air purge assembly 40 as well as the retrograde flow of free gases back into the blood stream.

As seen in FIG. 7, the hydrophobic filter 48 is attached to support frame 50 not shown, which prevents it from becoming displaced or damaged when exposed to positive or negative pressures. The hydrophobic filter 48 allows an increase in air bubble removal without increasing the amount of blood flow shunted away from the filters outlet port 36. The large diameter of the active air purge assembly 40 and hydrophobic filter 48 allows it to act as a pressure relief valve as any excess gas pressure entering through inlet port 32 is easily vented to atmosphere.

The hydrophobic filter 48 is adapted so that free gasses and not the blood within the filter comes in contact with the one-way valve 52. Air bubbles and debris within the blood flow which pass through the wetted pores of filter screens 62, 72 & 82 are directed into the active air purge assembly 40 where they come in contact with the hydrophobic filter 48. Air bubbles in contact with the hydrophobic filter 48 may be absorbed passively, or may be actively pulled from the blood using a suction source attached to the air removal port 44. The use of suction and the resulting negative pressure it creates above hydrophobic filter 48 ensures an active and more rapid absorption of air bubbles from the blood to further improve filter efficiency. Once through hydrophobic filter 48, free gases then cross the one-way valve 52 before being vented to the atmosphere through air removal port 44. A pressure monitoring port 45 is used to keep negative pressures within the active air purge assembly 40 at safe limits and within a user-defined range.

Moreover, by improving filter efficiency and micro-bubble clearance, the present invention also greatly reduces the potential risk of reaching the Bubble Point Pressure. This important feature results in a major accomplishment that in turn greatly reduces the need for large numbers of available wetted pores and thereby allows the use of a smaller micro-pore screen filter size to reduce the amount of foreign contact surface area and priming volume required. Additionally, the smaller screen surface area and lack of pleated filter material as described in the present invention will also help improve ease of priming and thereby promote better patient safety.

Blood filter system 10 was designed so that the active air purge assembly 40, downspout assembly 34 and hydrostatic pressure contained within an extracorporeal circuit work in unison to prevent the filter from becoming de-primed. To achieve this the active air purge assembly 40 at the filters top is designed to have a larger diameter opening then the inlet port 32 at the filters base, while the downspout assembly 34, which forms a sort of chamber at the filters center, is designed to retain hydrostatic pressure contained within the system to keep it fluid filled while in use. More specifically, the filters outlet port 34 is connected to the patient's circulation by way of tubing 17, or 22 as illustrated in FIG. 1. The result of this connection is that tubing 17, or 22 and downspout assembly 34 contain a hydrostatic pressure equal to the height difference between the patient's heart (tubing connection point) and the top of filters downspout assembly 34 (usually 25 to 30 cm H2O). If a sufficient volume of air were accidentally pumped into blood filter system 10 through inlet port 32 so that the space between filter housing 30 and rising inner wall 31 became air filled, the larger diameter of the active air purge assembly 40 would allow at least an equal volume of air to escape through hydrophobic filter 48 and purge port 42 to prevent air pressure within filter housing 30 from exceeding the hydrostatic pressure contained within downspout assembly 34. Thus, the hydrostatic pressure contained within the downspout assembly 34 ensures that the large diameter funnel 38, outflow tube 37, outlet port 36 and patient connection tubing 17, or 22 remain fluid filled, while excess air entering through the filters inlet port 32 is vented off through the active air purge assembly 40 and purge port 42. This feature of the present invention is unique to extracorporeal blood filtration devices and marks a first for improved patient safety by greatly reducing the risk of introducing gross air embolism to the patient. Together the above-mentioned achievements and features of the present invention combine to provide significant benefits over that of the prior art blood filters for extracorporeal circulations.

Figure 9:
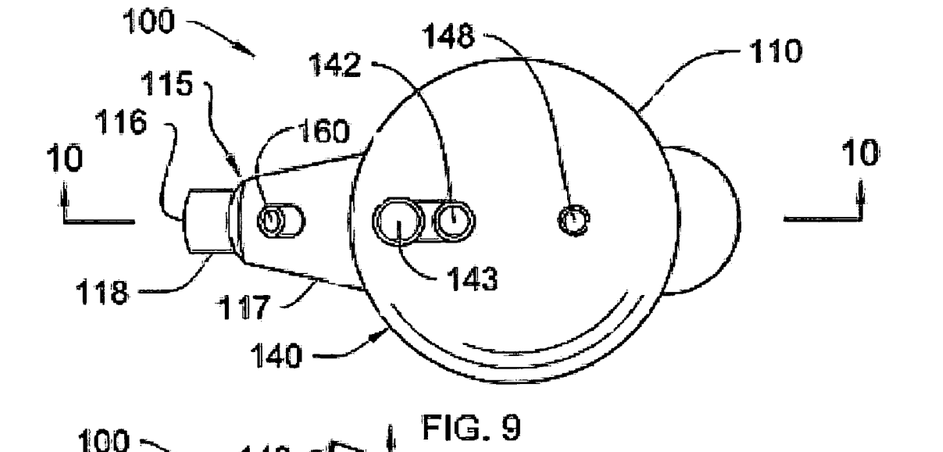
FIG. 9 is a top view of an alternate embodiment of the blood filter system of the present invention.
Figure 10:
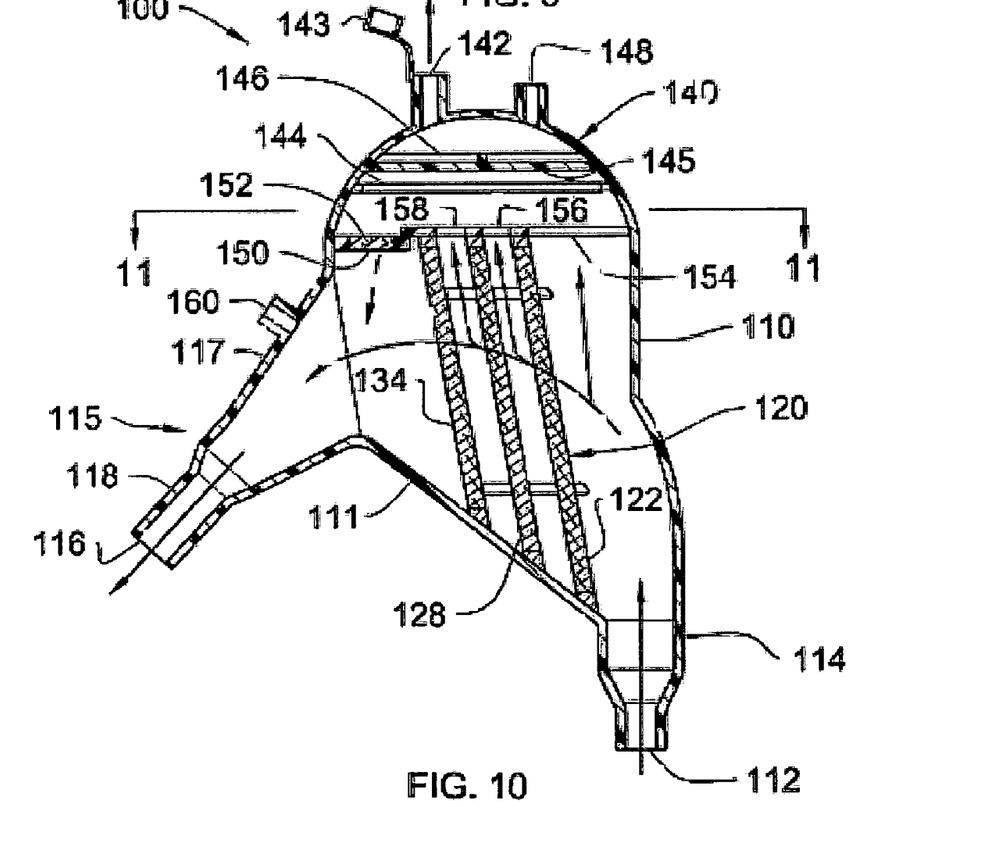
FIG. 10 is a cross-sectional view of an alternate embodiment of the blood filter system of the present invention taken along line 10 of FIG. 9

FIGS. 9 & 10 illustrate an alternate preferred embodiment of the present invention as blood filter system 100 and which comprises a filter housing 110, a rising inner wall 111, an inlet port 112, an inlet channel 114, a multi-stage sequential filter assembly 120, an active air purge assembly 140 and downspout assembly 115. The filter housing 110 can have a generally cylindrical configuration, but other configurations can also be used.

Figure 11:
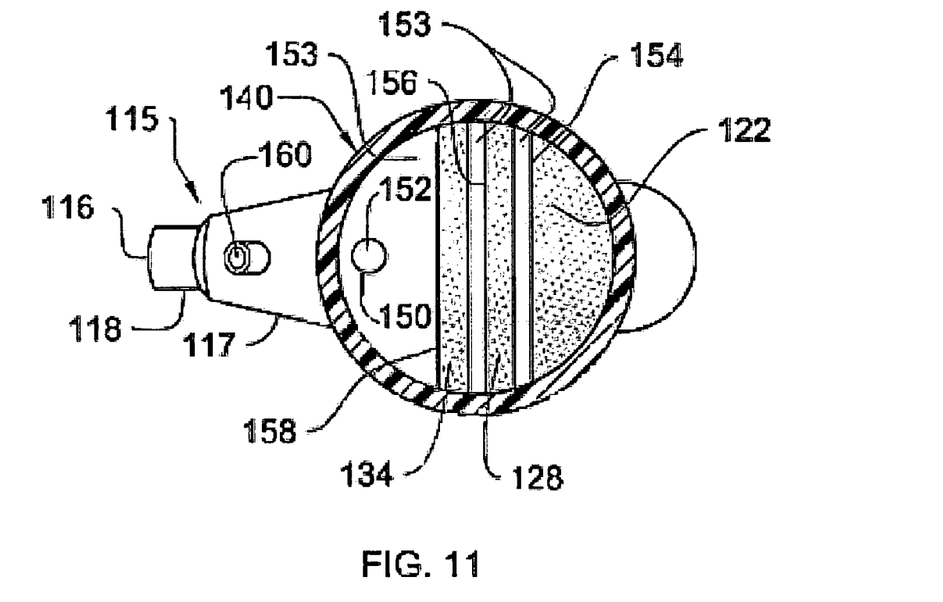
FIG. 11 is a cross-sectional view of an alternate embodiment of the blood filter system of the present invention taken along line 11 in FIG. 10.
Figure 12:
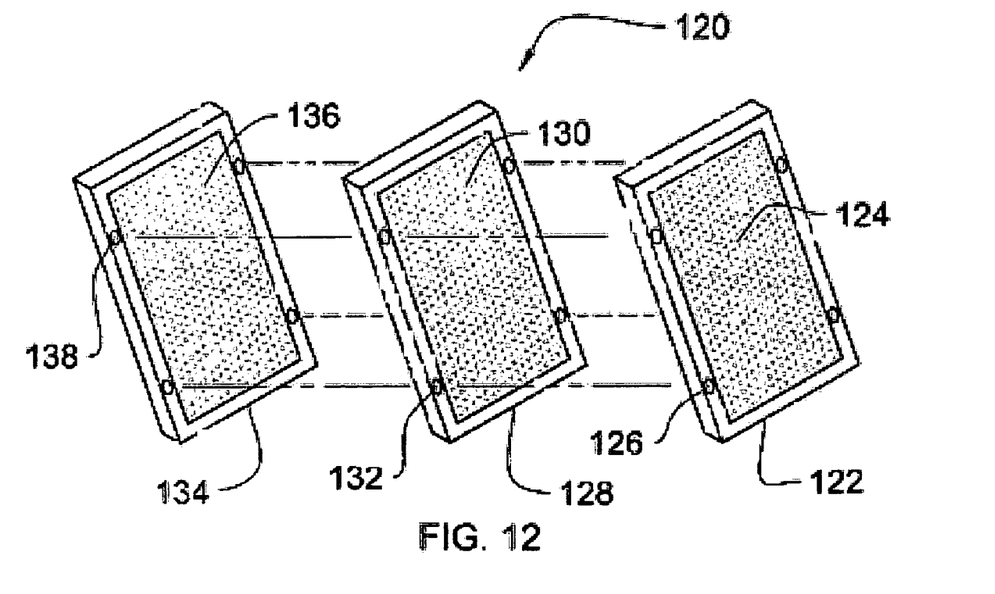
FIG. 12 is an exploded perspective view of an alternate embodiment of the sequential filter assembly of the present invention The same reference numerals refer to the same parts throughout the various figures.

As shown in FIGS. 10, 11 & 12 the multi-stage sequential filter assembly 120 can consist of a first stage filter 122, a second stage filter 128 and a third stage filter 134 all of which can rest on and be secured to each other, the rising inner wall 111 and bottom surface of the filter retaining ring 153. The active air purge assembly 140 can be positioned on top of filter housing 110 and may consist of inlet openings 154, 156 & 158, a purge port 150, a hydrophobic filter 144, a one-way valve 146, an air removal port 142 and a pressure monitoring port 148. The air removal port 142 may feature a tethered cap 143 which can be moved to close air removal port 142. The downspout assembly 115 can consist of a large diameter funnel 117, an outflow tube 118, and an outlet port 116. The outflow tube 118 extends down, connecting the bottom of the large diameter funnel 117 to outlet port 116.

As best illustrated in FIGS. 10, 11 & 12, the blood filter system 100 may contain a multi-stage sequential filter assembly 120 meant to achieve all the same principles of operation and advantages of use as previously described above for the multi-stage sequential filter assembly 60 of blood filter system 10.

As shown in FIG. 10, inlet port 112 with flared inlet channel 114 and downspout assembly 115 are designed and positioned in blood filter system 100 so that they achieve all the same principles of operation and advantages of use as previously described above for inlet port 32, inlet channel 33 and downspout assembly 34 of blood filter system 10.

As seen in FIG. 10, blood filter system 100 also features a unique up and down blood flow path meant to achieve all the same principles of operation and advantages of use as previously described above for blood filter system 10.

Also illustrated in FIGS. 10 & 11, the filter retaining ring 153 positioned above filters 122, 128 & 134 comprise defined openings 150, 154, 156 & 158 in fluid communication with the interior of filter housing 110. The active air purge assembly 140 further comprises a hydrophobic filter 144 in fluid communication with defined openings 150, 154, 156 & 158 of filter retaining ring 153, a one-way valve 146 in fluid communication with hydrophobic filter 144 and an air removal port 142 and pressure monitoring port 148 in fluid communication with the one-way valve 146.

Defined openings 154, 156 & 158 of filter retaining ring 153 allow blood carrying air bubbles and debris to enter the active air purge assembly 140 where they come in contact with hydrophobic filter 144 and are then removed.

The purge port 150 contains a micro-pore screen disk filter 152 positioned just after defined opening 158 which allows filtered blood to leave the active air purge assembly 140 and rejoin with the blood flow exiting blood filter system 100 through downspout assembly 115. The purge port 150 may also comprise a small diameter opening which provides a restriction to blood flow out of active air purge assembly 140 to ensure adequate time for air bubble removal through hydrophobic filter 144. The purge port 150 may be adapted so that it is recessed within the filter retaining ring 153 so as to keep its micro-pore screen disk filter 152 submerged within the blood at all times.

The hydrophobic filter 144 is adapted so that free gasses and not the blood within the filter housing 110 comes in contact with the one-way valve 146. Air bubbles and debris within the blood flow which cannot easily pass through the wetted pores of filter screens 124, 130 & 136 are swept up along the outside proximal surface of angled filters 122, 128 & 134 and directed into the active air purge assembly 140 through defined openings 154, 156 & 158 of filter retaining ring 153. Additionally, purge port 150 allows the negative pressure contained within a drainage circuit to be equally distributed throughout filter housing 110 and active air purge assembly 140 below the hydrophobic filter 144. This negative pressure augments the sweeping action created by the angled filters within the blood flow by actively drawing blood containing air bubbles and debris which cannot pass through the wetted pores up along the outside proximal surface of filters 122, 128 & 134 through defined openings 154, 156 & 158 of filter retaining ring 153 and into the active air purge assembly 140 where they come in contact with the hydrophobic filter 144 and are removed. Air bubbles in contact with the hydrophobic filter 144 may be absorbed passively or may be actively pulled from the blood using a suction source attached to the air removal port 142. The use of suction and the resulting negative pressure it creates above hydrophobic filter 144 ensures an active and more rapid absorption of air bubbles from the blood to further improve filter efficiency. Once passed the hydrophobic filter 144, free gases then cross the one-way valve 146 before being vented to the atmosphere through air removal port 142. A pressure monitoring port 148 is used to keep negative pressures within the active air purge assembly 140 at safe limits and within a user-defined range.

Moreover, blood filter system 100 uses all the same principles of operation and advantages of use to decrease the risk of reaching the bubble point pressure as previously described above for blood filter system 10. Also, blood filter system 100 incorporates the same design features as blood filter system 10 so that the active air purge assembly 140, downspout assembly 115 and hydrostatic pressure contained within the extracorporeal circuit work in unison as previously described above to prevent the blood filter system 100 from becoming de-primed.

Blood flow through filter system 100 passes through each filter stage 122, 128 & 134 in sequence, multiplying the barrier to air bubble and debris transfer to greatly improve blood filtration and filter efficiency. As long as the Bubble Point Pressure is not exceeded, the wetted pores of filter screens 124, 130 & 136 allow only blood to pass through while preventing the passage of air bubbles and debris. Any air bubbles and debris within the blood are directed up along the outside proximal surface of filter 122 through defined opening 154 of filter retaining ring 153 and into the active air purge assembly 140. In the event that the Bubble Point Pressure is exceeded and air is ejected across the micro-pore filter screen 124, they are then directed up along the outside proximal surface of filter 128 and through defined opening 156 of filter retaining ring 153 where they enter the active air purge assembly 140 to be removed. If the Bubble Point Pressure is again exceeded at filter 128, they are then directed up along the outside proximal surface of filter 134 and through defined opening 158 of filter retaining ring 153 then enter active air purge assembly 140 where they are expelled.

Both blood filter systems 10 and 100 posses unique features that together comprise a major advancement in blood filtration for extracorporeal circulations over that of the prior art including a smaller micro-pore screen filter contact surface area, reduced total device priming volume, unique shaped filter housing, unique up and down blood flow path, unique multi-stage sequential filter assembly, unique angled placement of micro-pore screen filters within the blood flow, unique sweeping action of blood flow on the micro-pore screen filters, reduced force of collision between air bubbles and angled screen filters, unique active air purge assembly, unique method of utilizing suction pressure to separate air bubbles from blood flow, unique pressure relief valve, unique downspout assembly, unique method of utilizing negative pressure within a venous drainage limb to augment air bubble and debris clearance and unique method of preventing the filter from becoming de-primed.

While the preferred embodiments of the blood filter system have been described in detail, it should be apparent that modifications which fall within the true spirit and scope of the invention are possible. With respect to the above description, it is realized that the optimum relationships for the parts of the invention including variations in size, materials, shape, form, function, manner of operation, assembly and use are deemed readily apparent and obvious to one skilled in the art and that all equivalent relationships to those illustrated in the drawings and described in the specification are intended to be encompassed by the present invention.

Therefore, the foregoing is to be considered only as illustrative of the principles and concepts of the present invention and that it is not desired to limit the invention to the exact construction and operation as shown and described.

I claim:

1. A method of removing free gas bubbles and debris from blood, the method comprising the steps of:
   a) introducing blood into the interior of a conical housing, said conical housing comprising:
   a purge port at the top of said conical housing; an active air purge assembly located below and in fluid communication with said purge port, said active air purge assembly comprising a hydrophobic filter, a one-way valve, an air removal port and a pressure monitoring port; at least a first microporous filter and a second microporous filter configured sequentially, wherein the top of said microporous filters are attached to a filter retaining ring with openings between attached portions of said microporous filters and in fluid communication with said purge port; and a microporous screen on top of a downspout assembly at the base of said conical housing;

b) moving blood through said microporous filters into the center of said conical housing;

c) removing a portion of gas from blood and said microporous filters and directing the portion of gas to openings in said filter retaining ring and through to said purge port;

e) pushing remaining gas in said conical housing through said active air purge assembly, wherein gas moves through said hydrophobic filter, and through said one-way valve, and then exits from said air removal port;

f) monitoring the pressure in said conical housing with said pressure monitoring port; and g) passing filtered and substantially gas-free blood out of said conical housing through said microporous screen and into said downspout assembly.

* * * * *